(12) United States Patent
Hwang et al.

(10) Patent No.: US 12,239,652 B2
(45) Date of Patent: Mar. 4, 2025

(54) COMPOSITION FOR PREVENTING OR TREATING MUSCULAR DISEASES, OR FOR IMPROVING MUSCULAR FUNCTIONS, CONTAINING GANGLIOSIDE

(71) Applicant: INDUSTRY-ACADEMIC COOPERATION FOUNDATION, YONSEI UNIVERSITY, Seoul (KR)

(72) Inventors: Jae Kwan Hwang, Seoul (KR); Seung Tae Su, Seoul (KR); Jong Wook Kim, Seoul (KR); Chang Hee Kim, Seoul (KR); Ji Hee Yoo, Gyeonggi-do (KR)

(73) Assignee: INDUSTRY-ACADEMIC COOPERATION FOUNDATION, YONSELUNIVERSITY, Seoul (KR)

( * ) Notice: Subject to any disclaimer, the term of this patent is extended or adjusted under 35 U.S.C. 154(b) by 830 days.

(21) Appl. No.: 17/271,031

(22) PCT Filed: Aug. 23, 2019

(86) PCT No.: PCT/KR2019/010800
§ 371 (c)(1),
(2) Date: Feb. 24, 2021

(87) PCT Pub. No.: WO2020/040615
PCT Pub. Date: Feb. 27, 2020

(65) Prior Publication Data
US 2021/0353659 A1    Nov. 18, 2021

(30) Foreign Application Priority Data

Aug. 24, 2018 (KR) .................. 10-2018-0099447
Aug. 23, 2019 (KR) .................. 10-2019-0103779

(51) Int. Cl.
| | | |
|---|---|---|
| A61K 31/7032 | (2006.01) | |
| A23L 33/00 | (2016.01) | |
| A23L 33/125 | (2016.01) | |
| A61K 31/739 | (2006.01) | |
| A61P 21/06 | (2006.01) | |

(52) U.S. Cl.
CPC ........ *A61K 31/7032* (2013.01); *A23L 33/125* (2016.08); *A23L 33/40* (2016.08); *A61K 31/739* (2013.01); *A61P 21/06* (2018.01); *A23V 2002/00* (2013.01)

(58) Field of Classification Search
CPC . A61K 31/7032; A61K 31/739; A23L 33/125; A61P 21/06; A61P 21/00; A23V 2200/316
See application file for complete search history.

(56) References Cited

U.S. PATENT DOCUMENTS

2010/0279985 A1    11/2010    Isogai

FOREIGN PATENT DOCUMENTS

| CA | 2070124 | | 12/1992 | |
|---|---|---|---|---|
| EP | 0433112 | A1 * | 6/1991 | ................ A61P 9/10 |
| JP | 2007131550 | | 5/2007 | |
| KR | 10-2016-0011422 | | 2/2016 | |
| WO | WO-2011028800 | A2 * | 3/2011 | ............. A61K 31/70 |

OTHER PUBLICATIONS

Iwamori, M., et al. Glycoconj. J. (2008) 25:675-683. (Year: 2008).*
Lee, H., et al., J. Agric. Food Chem. 2013, 61, 9689-9696. (Year: 2013).*
Wyatt, D. A., Anti-Aging Benefits of Bovine Colostrum. Center for Nutritional Research. Vital Health News. 2013 (Year: 2013).*
Prahm, K. P., et al. Neuromuscular Disorders. 27, (2017), 358-362. (Year: 2017).*
Mendonca, R. H., et al. Arq. Neuropsiquiatr. 2022; 80 (5 Suppl. 1): 249-256. (Year: 2022).*
Merriam-Webster.com. Prevent. 2023. Web. (Year: 2023).*
MedLinePlus. NIH. GM1 gangliosidosis. 2023. Web. (Year: 2023).*
Gorio, A., et al. Brain Research. 197, 1980, pp. 236-241. (Year: 1980).*
Leskawa, K. C., et al. Molecular and Cellular Biochemistry. 83:47-54. (Year: 1988).*
Paccalet, T., et al. PLoS ONE 5(4): e10055. (Year: 2010).*
Go, S., et al., "Altered expression of ganglioside GM3 molecular species and a potential regulatory role during myoblast differentiation," J. Biol. Chem., Apr. 28, 2017, 292(17):7040-7054.

* cited by examiner

*Primary Examiner* — Eric Olson
*Assistant Examiner* — Samuel L Galster
(74) *Attorney, Agent, or Firm* — DUANE MORRIS LLP; Gregory M. Lefkowitz; Brandon A. Chan

(57) ABSTRACT

The present invention relates to a composition for preventing or treating muscular diseases, or for improving muscular functions, containing gagnlioside. More specifically, the present invention relates to a pharmaceutical composition for preventing or treating muscular diseases, a food composition for preventing or alleviating muscular diseases, or a cosmetic composition for preventing or alleviating muscular diseases, all of which comprise gagnlioside, which can increase the expression of proteins associated with muscle protein synthesis and muscle mass growth in muscle cells and inhibit the expression of enzymes involved in muscle protein degradation at the mRNA level.

3 Claims, 9 Drawing Sheets
Specification includes a Sequence Listing.

[Fig. 1]
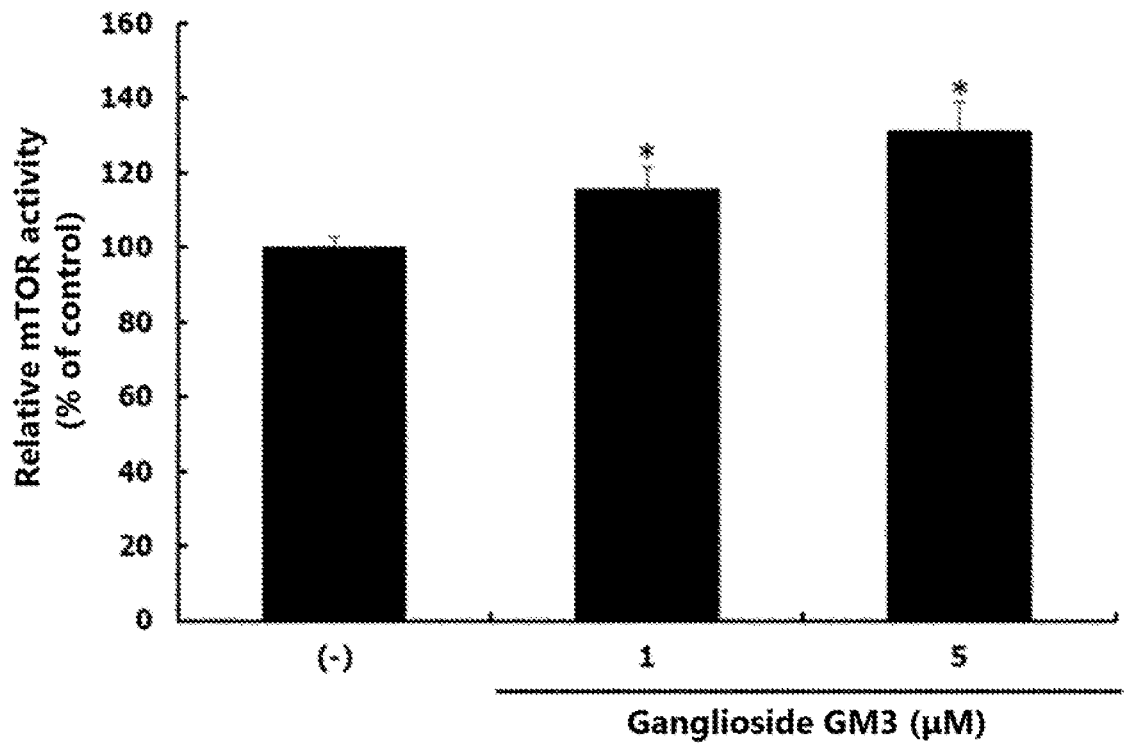
[Fig. 2]
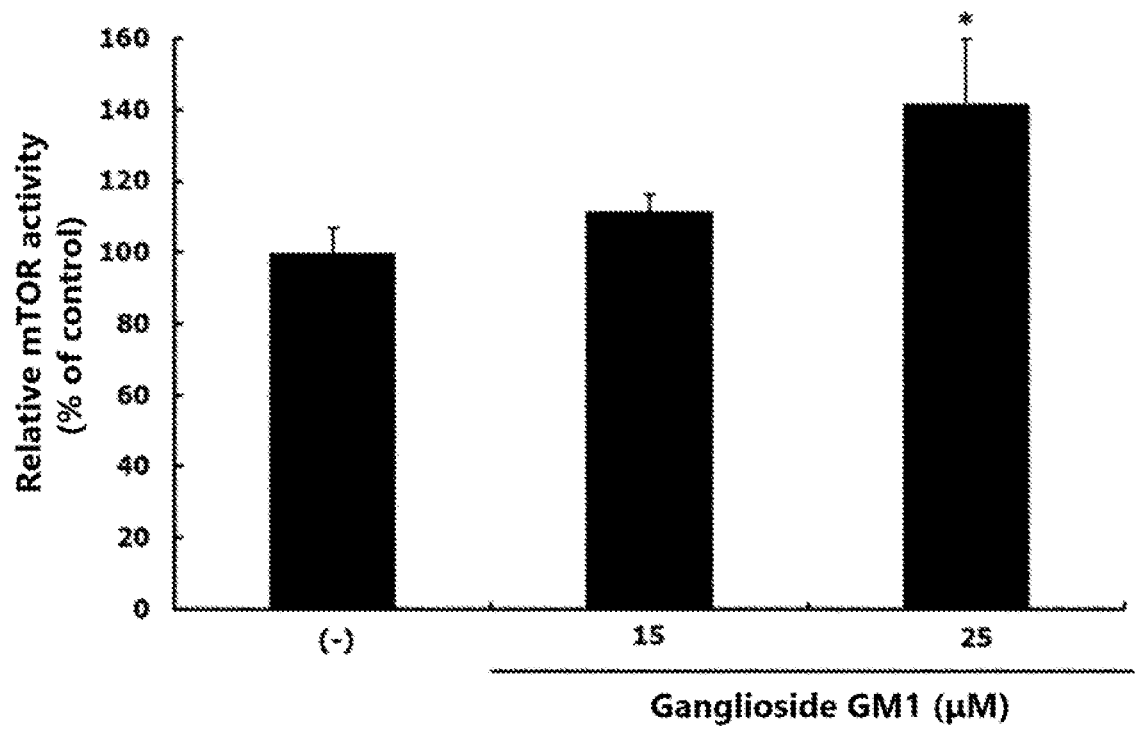

[Fig. 3]
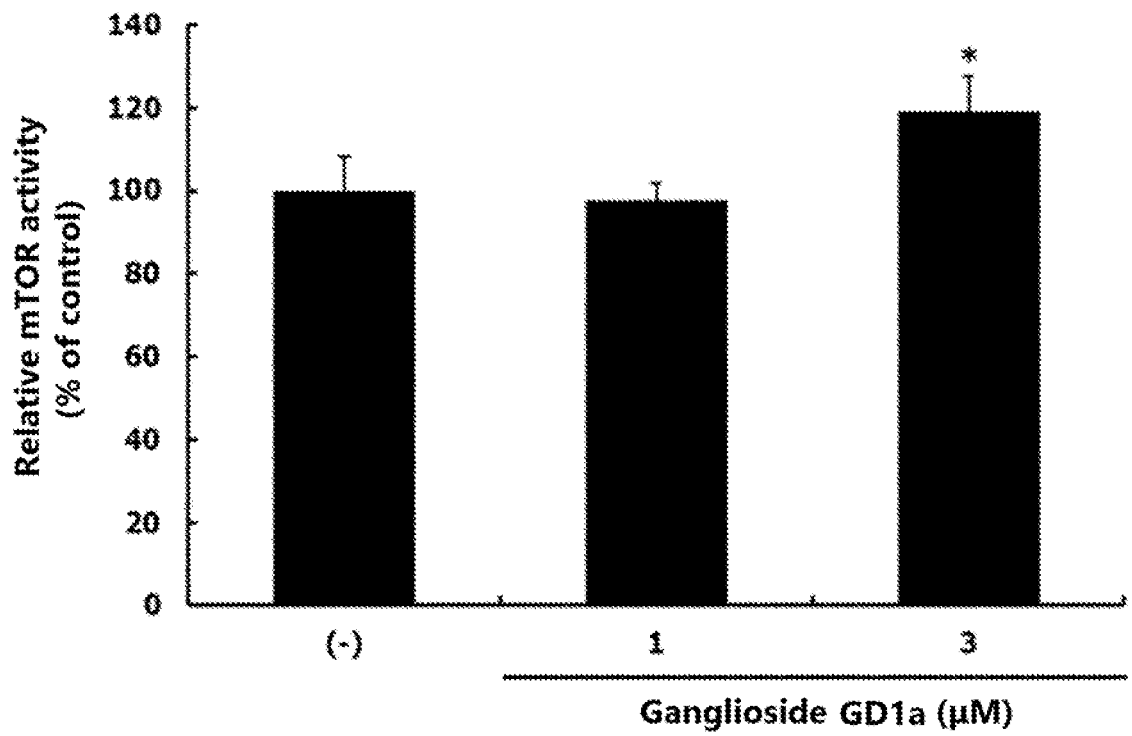
[Fig. 4]
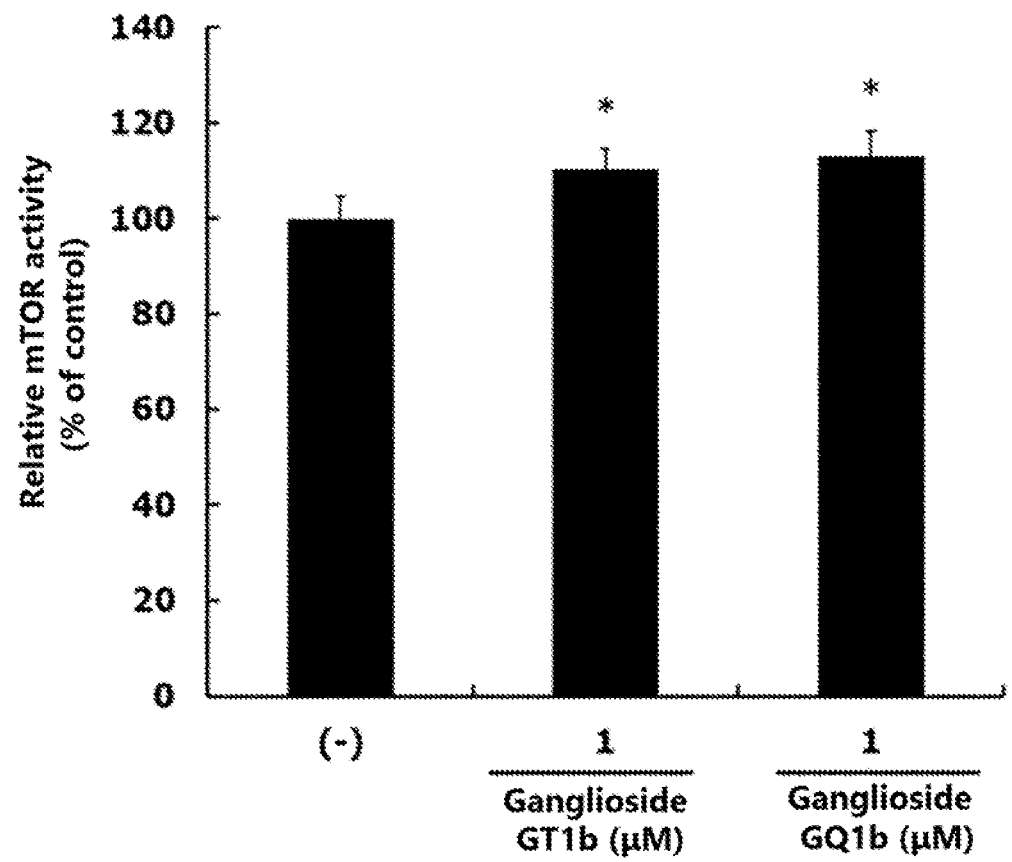

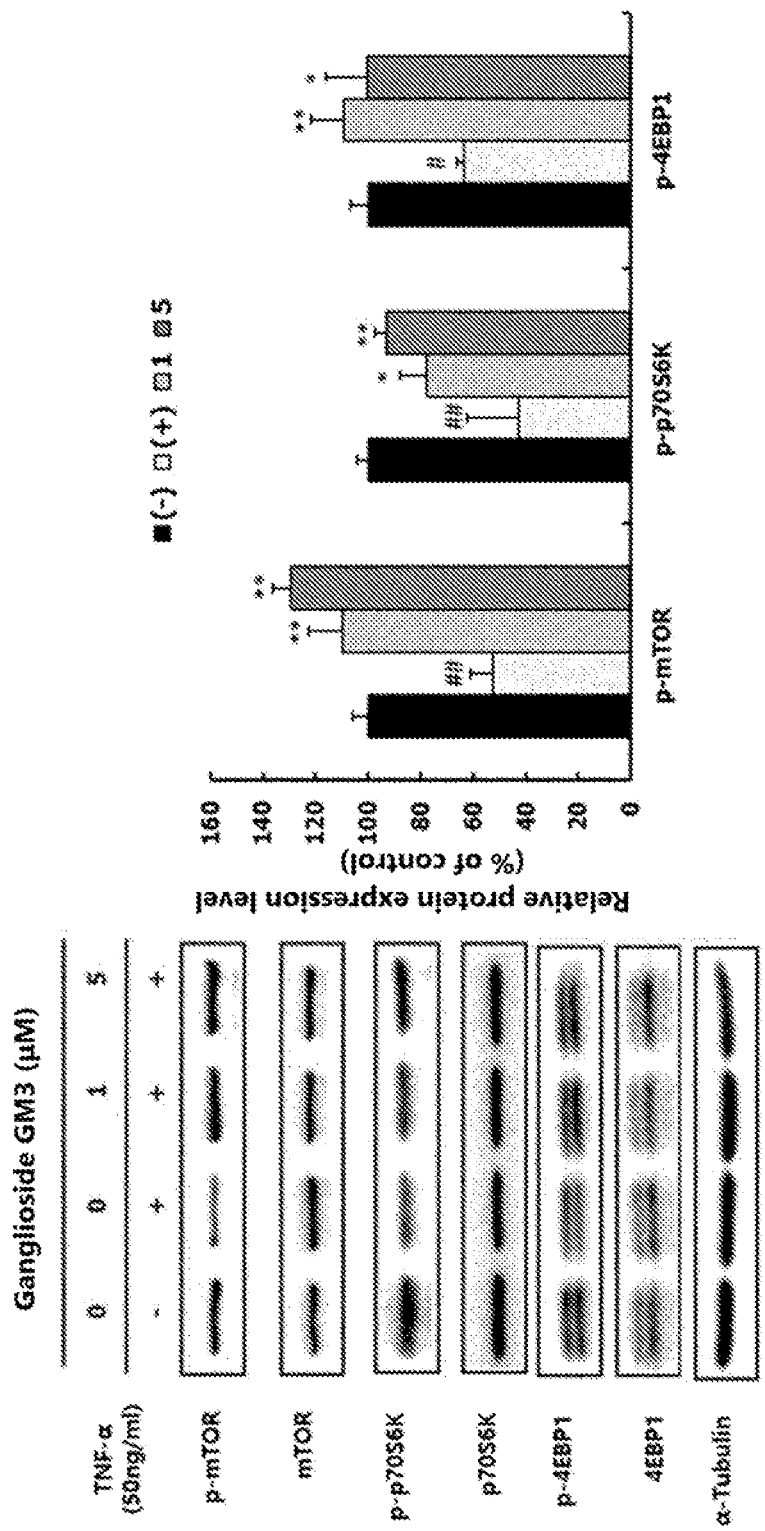
[Fig. 5]

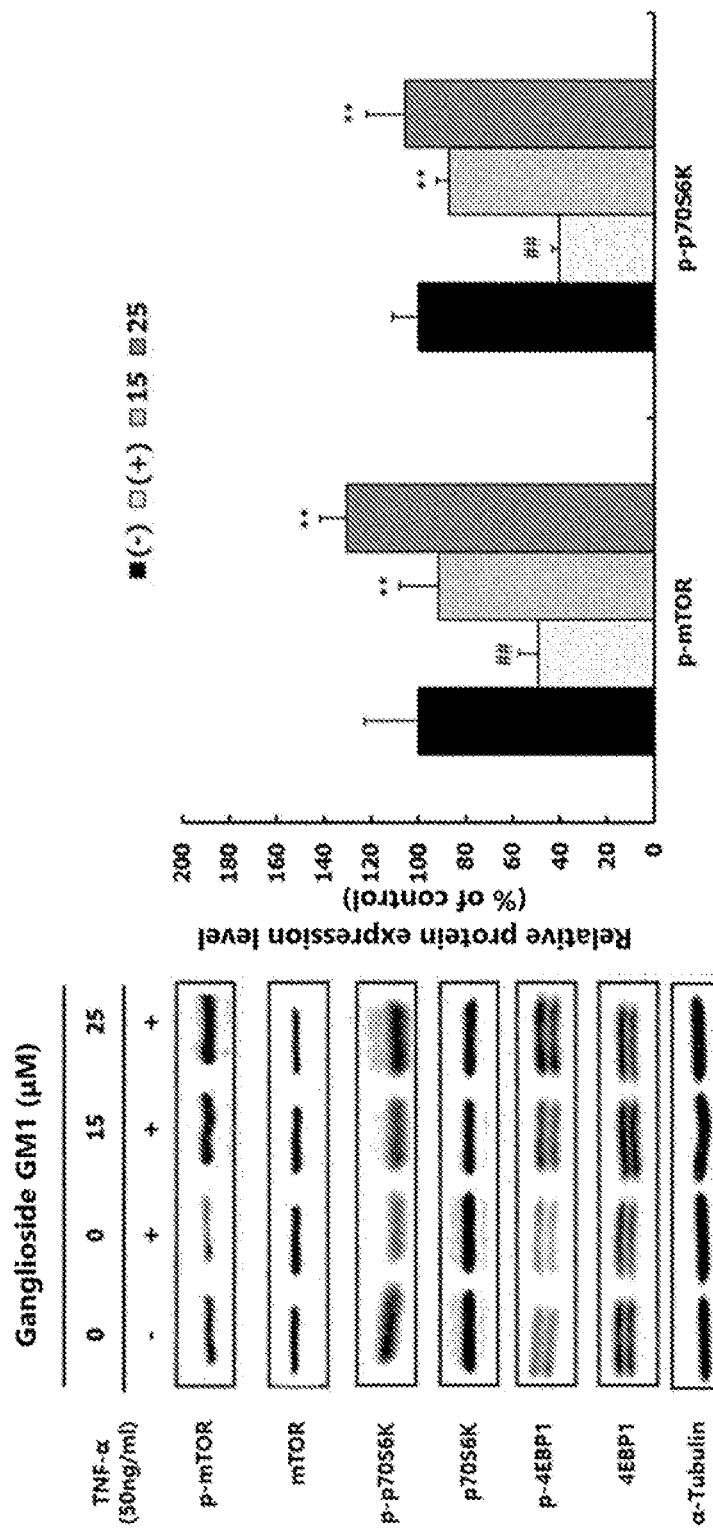
[Fig. 6]

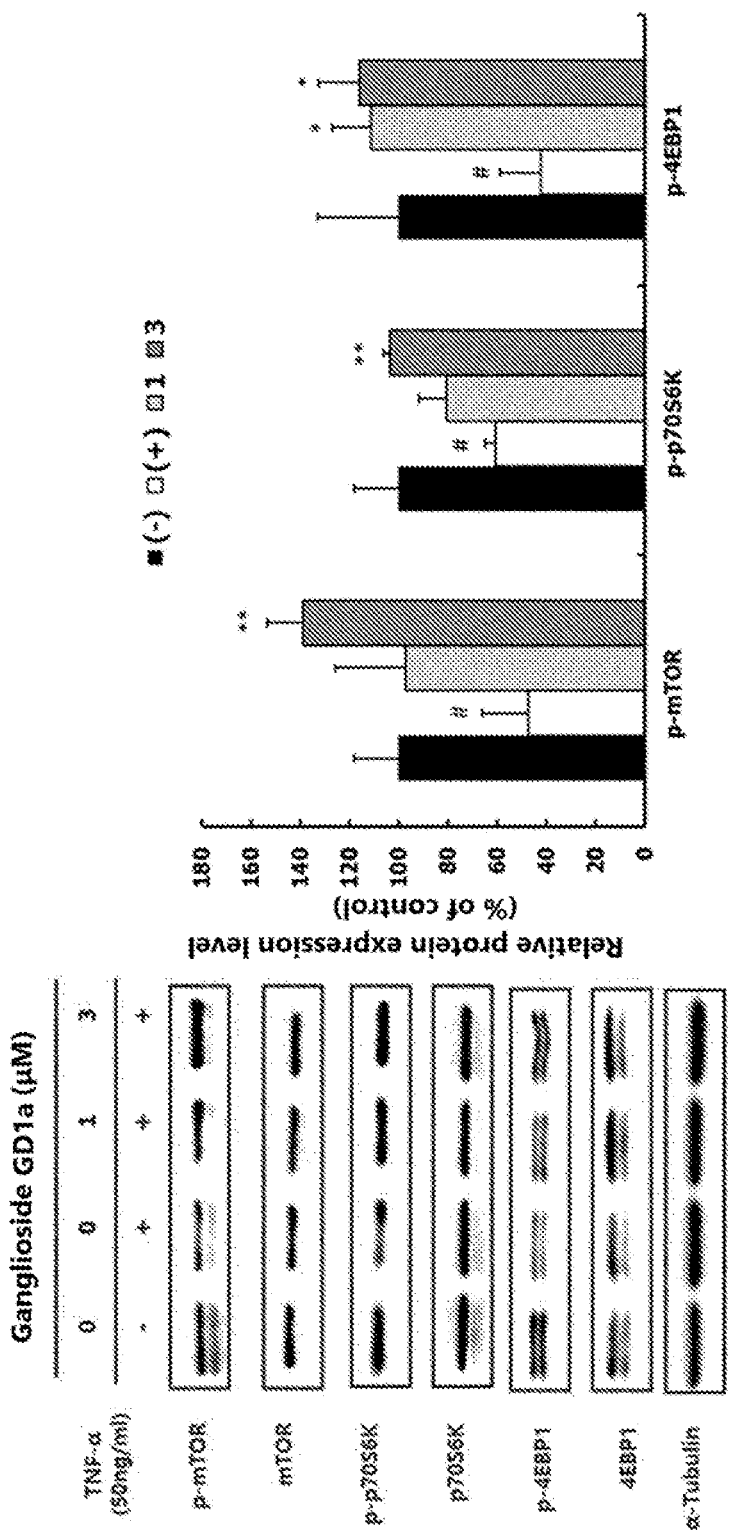
[Fig. 7]

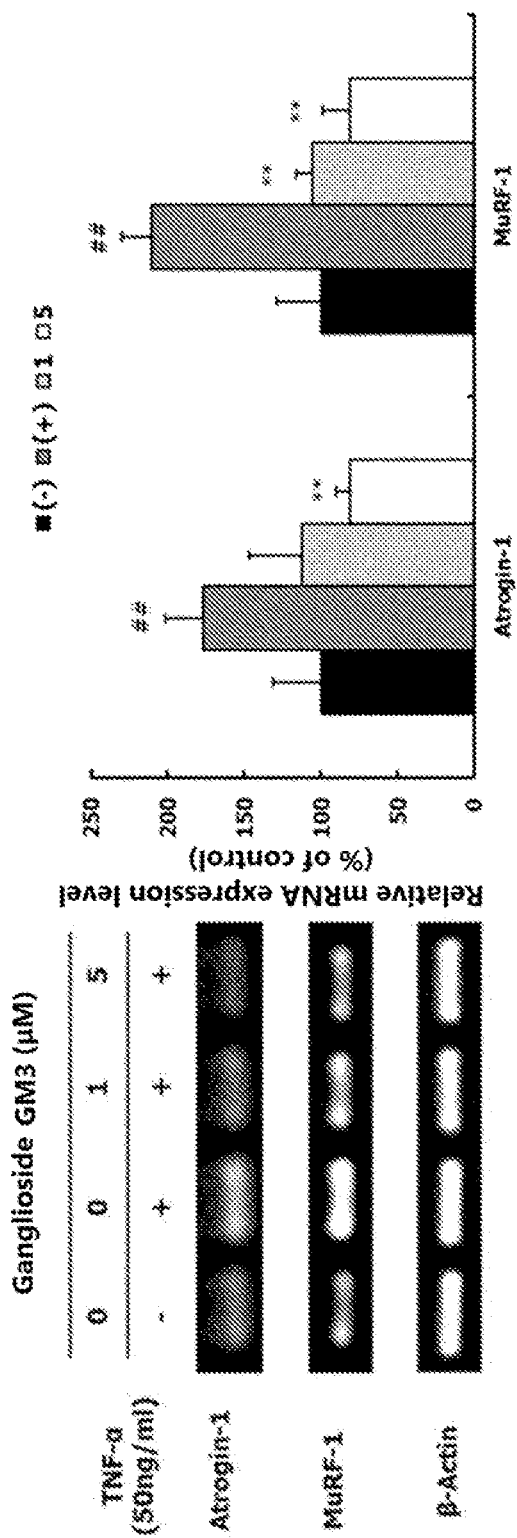
[Fig. 8]

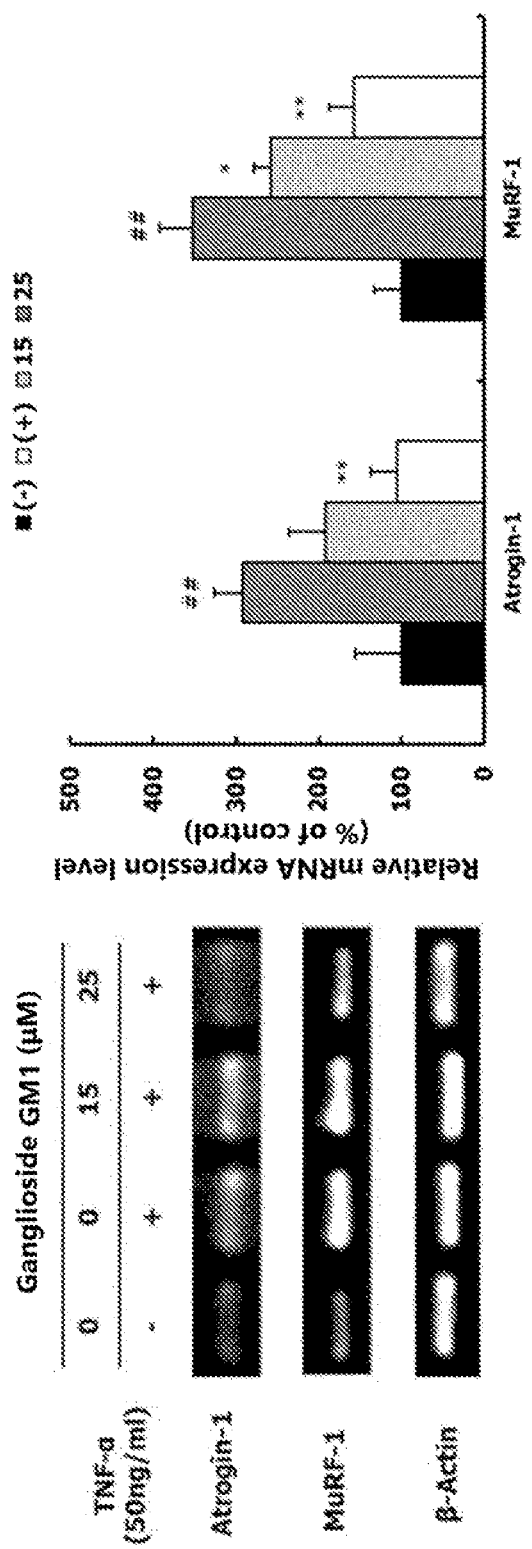
[Fig. 9]

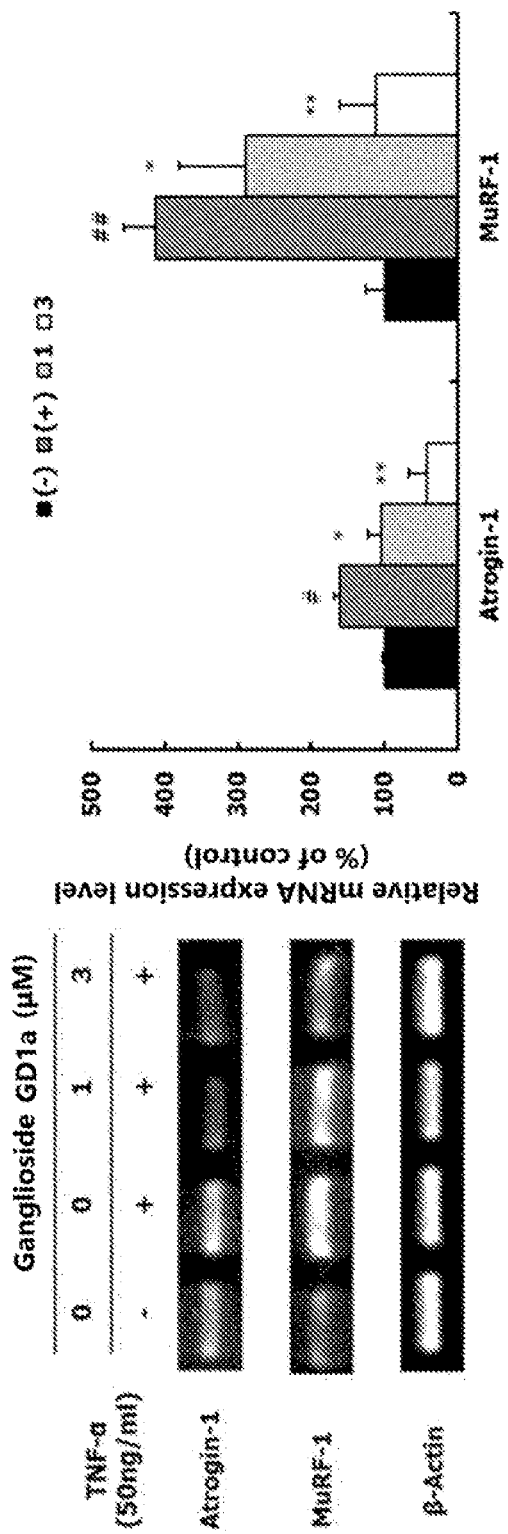
[Fig. 10]

[Fig. 11]
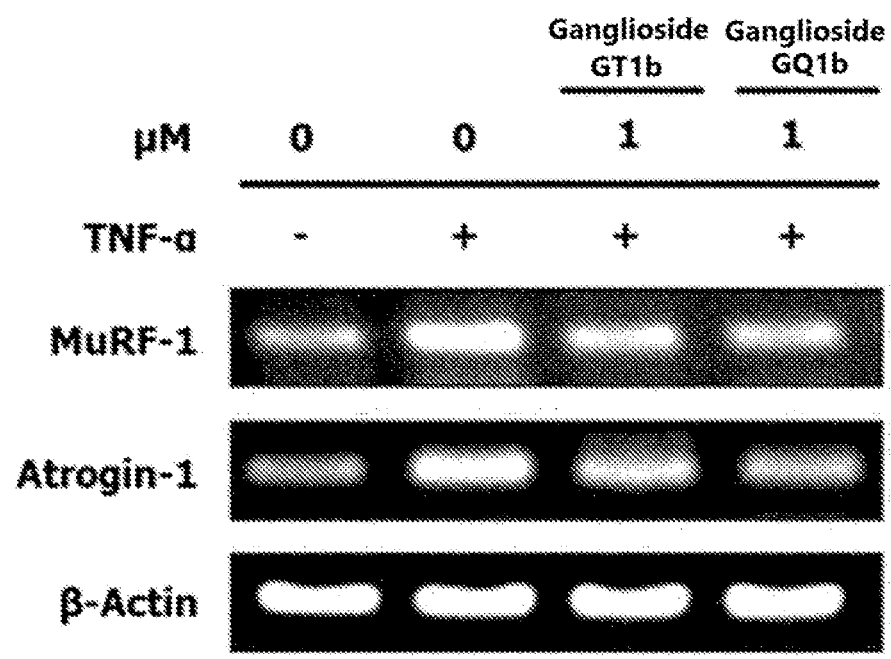

COMPOSITION FOR PREVENTING OR TREATING MUSCULAR DISEASES, OR FOR IMPROVING MUSCULAR FUNCTIONS, CONTAINING GANGLIOSIDE

CROSS-REFERENCE TO RELATED APPLICATIONS

This application is a § 371 national stage entry of International Application No. PCT/KR2019/010800, filed on Aug. 23, 2019, which claims priority to Korean Patent Application No. 10-2018-0099447, filed on Aug. 24, 2018, and Korean Patent Application No. 10-2019-0103779, filed on Aug. 23, 2019, the entire contents of which are incorporated herein by reference.

SEQUENCE LISTING

The instant application contains a Sequence Listing, which has been submitted electronically in ASCII format, and is hereby incorporated by reference in its entirety. Said ASCII copy, created on Jul. 8, 2021, is named G1035-18801_RevisedSeqList.txt and is 1,549 bytes in size.

TECHNICAL FIELD

The present invention relates to compositions for preventing or treating a muscle disease or improving muscle functions including a ganglioside. More specifically, the present invention relates to a pharmaceutical composition for preventing or treating a muscle disease, a food composition for preventing or ameliorating a muscle disease, and a cosmetic composition for preventing or ameliorating a muscle disease, each of which includes a ganglioside.

BACKGROUND ART

Muscular atrophy refers to a progressive decline in muscle mass that leads to muscle weakness and degeneration (Cell, 119(7): 907-910, 2004). Muscular atrophy is exacerbated by inactivity, oxidative stress, and chronic inflammation and results in poor muscle functions and athletic performance (Clinical Nutrition, 26(5): 524-534, 2007). Muscle mass is the most important factor determining muscle functions and is maintained by a balance between protein synthesis and degradation. Muscular atrophy occurs when protein breakdown exceeds protein synthesis (The International Journal of Biochemistry and Cell Biology, 37(10): 1985-1996, 2005).

Muscle size is regulated by intracellular signaling pathways responsible for the induction of anabolism or catabolism in muscle. When the signaling pathway inducing muscle protein synthesis is more dominant than that inducing muscle protein breakdown, the increased muscle protein synthesis leads to an increase in muscle size (hypertrophy) or an increase in the number of myofibers (hyperplasia) (The Korea Journal of Sports Science, 20(3): 1551-1561, 2011).

Factors involved in muscle protein synthesis phosphorylate downstream proteins via stimulation of the phosphatidylinositol-3 kinase (PI3K)/Akt pathway to induce protein synthesis in muscle cells. The activity of the mammalian target of rapamycin (mTOR) caused by PI3K/Akt signaling is recognized as a key growth signaling factor that integrates various growth signals in cells. mTOR activates 4E-binding protein (4EBP1) and phosphorylated 70-kDa ribosomal S6 kinase (p70S6K), which are two factors that initiate mRNA translation, to induce muscle protein synthesis, contributing to an increase in muscle mass (The Korea Journal of Sports Science, 20(3): 1551-1561, 2011; The International Journal of Biochemistry and Cell Biology, 43(9): 1267-1276, 2011). Conversely, migration of the transcription factor forkhead box (FoxO) from the cytoplasm to the nucleus increases the expression of the E3 ubiquitin ligase factors atrogin-1 and MuRF1 involved in protein degradation (Disease Models and Mechanisms, 6: 25-39, 2013). The increased expression levels of atrogin-1 and MuRF1 lead to the acceleration of proteolysis in muscle, resulting in a decline in muscle mass. Accordingly, promotion of mTOR activity and inhibition of atrogin-1 and MuRF1 expression increase the amount of muscle protein, leading to an increase in muscle mass.

Gangliosides, a class of glycosphingolipids, are amphoteric glycolipids composed of a hydrophilic glycan chain and a hydrophobic ceramide moiety and having one or more sialic acids or N-acetylneuraminic acids (NANA). Gangliosides are classified into different classes based on the number of sialic acids present. In ganglioside nomenclature, the prefix G refers to ganglio, the second letter refers to the number of sialic acid residues (mono, di, tri, etc.), and the Arabic numerals (1, 2, 3) refer to the order of migration of the gangliosides on thin layer chromatograms (TLC). Terms such as GD1a, GT1b, etc. were added to indicate modifications to the basic structure (Essentials of Glycobiology. 3rd edition, chapter 11, 2017). Gangliosides are found in central nervous tissues and are involved in neural functions and numerous functions of the cell membranes (Journal of Oleo Science, 60(10): 537-544, 2011). Gangliosides are also known to have functions of reducing cancer cells to normal cells (Clinical and Developmental Immunology, 2010: 814397) and to be effective against obesity (FEBS Letter, 589: 3221-3227, 2015) and inflammation (International Immunopharmacology, 28(1): 136-145, 2015). However, to the best of our knowledge, little is known about the ability of gangliosides to prevent or treat muscle diseases or improve muscle functions.

The present inventors have made an effort to develop therapeutic agents for diseases associated with muscle dysfunction such as muscular atrophy that have increased regulatory activity on muscle function and are safely applicable. As a result, the present inventors have found that some gangliosides can be used as active ingredients of compositions for preventing or treating muscle diseases or improving muscle functions due to their ability to increase the expression of proteins associated with muscle protein synthesis in muscle cells and an increase in muscle mass and inhibit the expression of enzymes involved in muscle protein degradation at the mRNA level. The present invention has been accomplished based on this finding.

DETAILED DESCRIPTION OF THE INVENTION

Problems to be Solved by the Invention

One object of the present invention is to provide a pharmaceutical composition for preventing or treating a muscle disease including a ganglioside as an active ingredient.

A further object of the present invention is to provide a food composition for preventing or ameliorating a muscle disease including a ganglioside as an active ingredient.

Another object of the present invention is to provide a cosmetic composition for preventing or ameliorating a muscle disease including a ganglioside as an active ingredient.

Means for Solving the Problems

The present invention provides a pharmaceutical composition for preventing or treating a muscle disease including a ganglioside as an active ingredient.

The present invention also provides a food composition for preventing or ameliorating a muscle disease including a ganglioside as an active ingredient.

The present invention also provides a cosmetic composition for preventing or ameliorating a muscle disease including a ganglioside as an active ingredient.

According to one preferred embodiment of the present invention, the ganglioside may be represented by Formula 1:

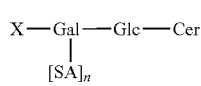

[Formula 1]

wherein X is absent, GalNAc, or Y-Gal-GalNAc, Y is $[SA]_m$, Gal is galactose, Glc is glucose, Cer is ceramide, GalNAc is N-acetylgalactosamine, SA is sialic acid, n is an integer from 1 to 3, and m is an integer from 0 to 2.

According to one preferred embodiment of the present invention, the ganglioside of Formula 1 may be selected from ganglioside GM3, ganglioside GM1, ganglioside GD1a, ganglioside GT1b, and ganglioside GQ1b.

According to one preferred embodiment of the present invention, the ganglioside may be extracted, concentrated or separated from antler, sweet potato, colostrum, milk or a mixture thereof.

According to another preferred embodiment of the present invention, the muscle disease may be caused by muscle dysfunction, muscle wasting or muscle degeneration and may be selected from the group consisting of atony, muscular atrophy, muscular dystrophy, muscle degeneration, myasthenia gravis, cachexia, age-related sarcopenia, and combinations thereof.

The present invention also provides a novel use of a ganglioside in the manufacture of a medicament for preventing or treating a muscle disease.

The present invention also provides a method for treating a muscle disease including administering a pharmaceutical composition including a ganglioside as an active ingredient to a patient suffering from a muscle disease.

Effects of the Invention

The compositions of the present invention, each of which includes a ganglioside as an active ingredient, are effective in preventing or treating a muscle disease or improving muscle functions.

The ganglioside as an active ingredient in the compositions of the present invention is effective in increasing muscle mass in a patient suffering from a muscle disease caused by muscle dysfunction, muscle wasting or muscle degeneration due to its ability to increase the expression of proteins associated with muscle protein synthesis in muscle cells and an increase in muscle mass and inhibit the expression of enzymes involved in muscle protein degradation at the mRNA level.

BRIEF DESCRIPTION OF THE DRAWINGS

FIG. 1 shows the activities of mTOR in L6 muscle cells when treated with different concentrations of ganglioside GM3.

FIG. 2 shows the activities of mTOR in L6 muscle cells when treated with different concentrations of ganglioside GM1.

FIG. 3 shows the activities of mTOR in L6 muscle cells when treated with different concentrations of ganglioside GD1a.

FIG. 4 shows the activities of mTOR in L6 muscle cells when treated with gangliosides GT1b and GQ1b.

FIG. 5 shows the protein expression levels of p-mTOR, p-p70S6K, and p-4EBP1 as biomarkers related to mRNA translation in L6 muscle cells when treated with different concentrations of ganglioside GM3.

FIG. 6 shows the protein expression levels of p-mTOR, p-p70S6K, and p-4EBP1 as biomarkers related to mRNA translation in L6 muscle cells when treated with different concentrations of ganglioside GM1.

FIG. 7 shows the protein expression levels of p-mTOR, p-p70S6K, and p-4EBP1 as biomarkers related to mRNA translation in L6 muscle cells when treated with different concentrations of ganglioside GD1a.

FIG. 8 shows the mRNA expression levels of atrogin-1 and MuRF1 in L6 muscle cells when treated with different concentrations of ganglioside GM3.

FIG. 9 shows the mRNA expression levels of atrogin-1 and MuRF1 in L6 muscle cells when treated with different concentrations of ganglioside GM1.

FIG. 10 shows the mRNA expression levels of atrogin-1 and MuRF1 in L6 muscle cells when treated with different concentrations of ganglioside GD1a.

FIG. 11 shows the mRNA expression levels of atrogin-1 and MuRF1 in L6 muscle cells when treated with gangliosides GT1b and GQ1b.

MODE FOR CARRYING OUT THE INVENTION

The present invention will now be described in detail.

Some gangliosides are effective as active ingredients of compositions for preventing or treating muscle diseases due to their ability to increase the expression of proteins associated with muscle protein synthesis in muscle cells and an increase in muscle mass and inhibit the expression of enzymes involved in muscle protein degradation at the mRNA level.

Gangliosides, a class of glycosphingolipids, are amphoteric glycolipids composed of a hydrophilic glycan chain and a hydrophobic ceramide moiety and having one or more sialic acids.

Gangliosides may be represented by Formula 1:

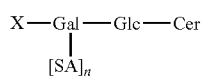

[Formula 1]

wherein X is absent, GalNAc, or Y-Gal-GalNAc, Y is $[SA]_m$, Gal is galactose, Glc is glucose, Cer is ceramide, GalNAc is N-acetylgalactosamine, SA is sialic acid, n is an integer from 1 to 3, and m is an integer from 0 to 2.

The gangliosides of Formula 1 may be selected from ganglioside GM3, ganglioside GM1, ganglioside GD1a, ganglioside GT1b, and ganglioside GQ1b.

Gangliosides with one sialic acid include GM1, GM2, and GM3. As an example, ganglioside GM3 has the structure represented by Formula 2:

[Formula 2]

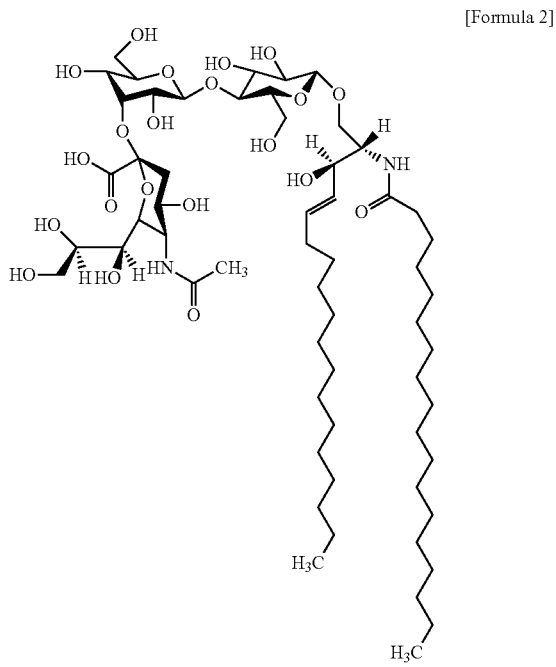

As another example, ganglioside GM1 has the structure represented by Formula 3:

[Formula 3]

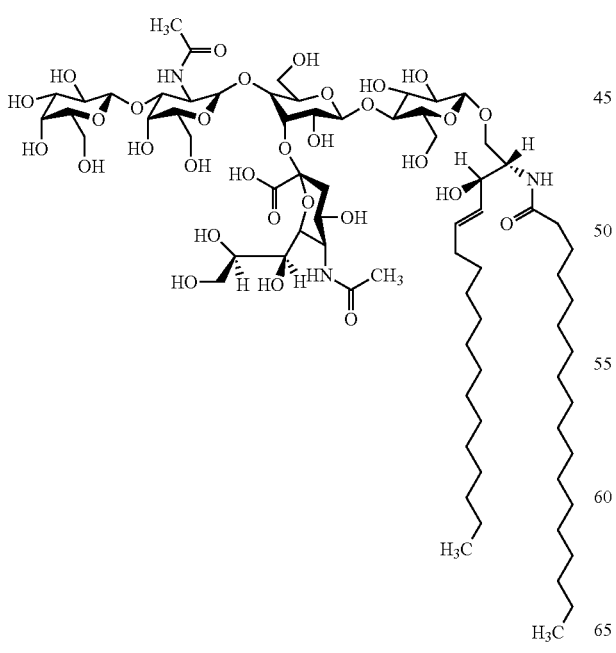

Gangliosides with two sialic acids include GD1a, GD1b, GD2, and GD3. For example, ganglioside GD1a has the structure represented by Formula 4:

[Formula 4]

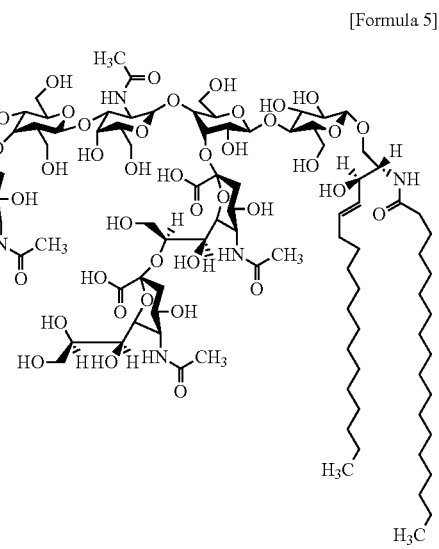

Gangliosides with three sialic acids include GT1a, GT1b, and GT3. For example, ganglioside GT1b has the structure represented by Formula 5:

[Formula 5]

Gangliosides with four sialic acids include GQ1a and GQ1b. For example, ganglioside GQ1b has the structure represented by Formula 6.

[Formula 6]

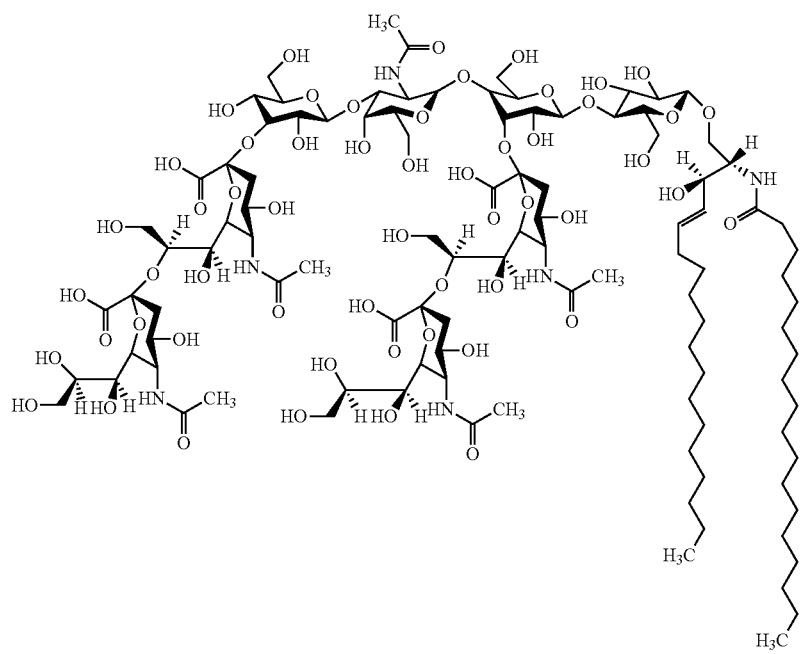

Gangliosides may be extracted, concentrated or separated from natural sources, artificially synthesized or commercially available. Gangliosides are preferably derived from natural sources selected from the group consisting of antler, sweet potato, colostrum, and milk.

As used herein, the term "muscle disease" refers to a disease caused by muscle dysfunction, muscle wasting or muscle degeneration, preferably a disease reported in the literature. Specifically, the muscle disease is preferably selected from the group consisting of, but not limited to, atony, muscular atrophy, muscular dystrophy, muscle degeneration, myasthenia gravis, cachexia, age-related sarcopenia, and combinations thereof.

The muscle wasting or degeneration occurs due to genetic factors, acquired factors, aging, and other factors. The muscle wasting is characterized by a gradual loss of muscle mass or weakness and degeneration of muscles, particularly skeletal or voluntary muscles and cardiac muscles.

More specifically, the term "muscle" refers collectively to sinews, muscles, and tendons. The term "muscle function" refers to the ability of muscle to exert its force when contracted and is intended to include muscular strength, muscular endurance, and agility. The muscular strength means the ability of muscle to exert its maximum contractile force to overcome resistance, the muscular endurance means the ability of muscle to show how long or how many times it can be repeatedly contracted and relaxed for a given weight, and the agility means the ability of muscle to exert its strong force in a short time. These muscle functions are controlled by the liver and are proportional to muscle mass. The expression "improving muscle functions" means that muscle functions are better enhanced.

In the Examples section that follows, the present inventors have tried to determine the activity of gangliosides in muscle cells, and as a result, found that gangliosides increased the expression of proteins associated with muscle protein synthesis and an increase in muscle mass (FIGS. 1 to 7).

In the Examples section that follows, the present inventors have also tried to determine the activity of gangliosides in muscle cells, and as a result, found that gangliosides reduced the expression of enzymes MuRF1 and atrogin-1 involved in muscle protein degradation at the mRNA level (FIGS. 8-11).

The present invention provides compositions for preventing or treating a muscle disease or improving muscle functions including a ganglioside and optionally one or more active ingredients having similar functions to the ganglioside. The presence of the additional ingredients can further enhance the effects of the compositions on improving muscle functions. When the ingredients are added, skin safety, ease of formulation, and stability of the active ingredients would have to be taken into consideration according to the combined use.

Due to its ability to increase the expression of proteins associated with muscle protein synthesis in muscle cells and an increase in muscle mass and inhibit the expression of enzymes involved in muscle protein degradation at the mRNA level, the ganglioside is effective in increasing muscle mass in a patient suffering from a muscle disease caused by muscle dysfunction, muscle wasting or muscle degeneration, thus being suitable as an active ingredient in a pharmaceutical composition for preventing or treating the muscle disease.

Specifically, the present invention provides a pharmaceutical composition for preventing or treating a muscle disease including a ganglioside or a pharmaceutically acceptable salt thereof. As used herein, the term "pharmaceutically acceptable salt" refers to a salt that is physiologically acceptable and does not usually cause allergic responses or their similar responses when administered to humans. The salt is preferably an acid addition salt formed by a pharmaceutically acceptable free acid.

The pharmaceutically acceptable salt of the ganglioside may be an acid addition salt formed using an organic or inorganic acid. Examples of suitable organic acids include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, p-toluenesulfonic acid, and methanesulfonic acid. Examples of suitable inorganic acids include hydrochloric acid, hydrobromic acid, sulfuric acid, phosphoric acid, nitric acid, carbonic acid, and boric acid. The acid addition salt is preferably in the form of a hydrochloride or acetate, more preferably a hydrochloride.

The acid addition salt is prepared by a suitable method known in the art, for example, by a) directly mixing the ganglioside with an appropriate acid, b) dissolving the mixture in a solvent or hydrous solvent, followed by mixing, or c) placing the ganglioside in an acid in a solvent or hydrous solvent, followed by mixing.

Other salts of the ganglioside are also possible. Examples of such salts include GABA, gabapentin, pregabalin, nicotinate, adipate, hemimalonate, cysteine, acetylcysteine, methionine, arginine, lysine, ornithine, and aspartate salts.

The pharmaceutical composition of the present invention may further include one or more pharmaceutically acceptable carriers.

Examples of the pharmaceutically acceptable carriers include carriers for oral administration and carriers for parenteral administration. Examples of suitable carriers for oral administration include lactose, starch, cellulose derivatives, magnesium stearate, and stearic acid. Examples of suitable carriers for parenteral administration include water, suitable oils, saline, aqueous glucose, and glycols. The pharmaceutical composition may further include a stabilizer and a preservative. Suitable stabilizers are antioxidants such as sodium hydrogen sulfite, sodium sulfite, and ascorbic acid. Suitable preservatives are benzalkonium chloride, methyl paraben, propyl paraben, and chlorobutanol. Other pharmaceutically acceptable carriers can be found in Remington's Pharmaceutical Sciences, 19th ed., Mack Publishing Company, Easton, PA, 1995.

The pharmaceutical composition of the present invention may be administered to mammals, including humans, by any appropriate route of administration, for example, orally or parenterally. Examples of parenteral routes of administration include, but are not limited to, intravenous, intramuscular, intraarterial, intramedullary, intradural, intracardiac, transdermal, subcutaneous, intraperitoneal, intranasal, gastrointestinal, topical, sublingual, and intrarectal routes.

The pharmaceutical composition of the present invention may be formulated into a preparation for oral or parenteral administration depending on the route of administration. The pharmaceutical composition of the present invention may be formulated with one or more additives selected from buffers (e.g., saline or PBS), antioxidants, bacteriostatic agents, chelating agents (e.g., EDTA or glutathione), fillers, extenders, binders, adjuvants (e.g., aluminum hydroxide), suspending agents, thickeners, wetting agents, disintegrants, surfactants, diluents, and excipients.

Solid preparations for oral administration include tablets, pills, powders, granules, liquids, gels, syrups, slurries, suspensions, and capsules. Such solid preparations can be prepared by mixing the pharmaceutical composition of the present invention with one or more excipients, for example, starches (including corn starch, wheat starch, rice starch, and potato starch), calcium carbonate, sucrose, lactose, dextrose, sorbitol, mannitol, xylitol, erythritol, maltitol, cellulose, methyl cellulose, sodium carboxymethyl cellulose, hydroxypropyl methylcellulose, and gelatin. For example, tablets or dragees may be obtained by blending the active ingredient with one or more solid excipients, grinding the blend, adding one or more suitable adjuvants thereto, and processing the mixture into granules.

In addition to the simple excipients, lubricating agents such as magnesium stearate and talc may also be used. Liquid preparations for oral administration are suspensions, solutions for internal use, emulsions, and syrups. The liquid preparations may include various excipients such as wetting agents, sweeteners, aromatic substances, and preservatives, as well as simple diluents known in the art such as water or liquid paraffin.

The pharmaceutical composition of the present invention may optionally further include cross-linked polyvinylpyrrolidone, agar, alginic acid or sodium alginate as a disintegrant. The pharmaceutical composition of the present invention may further include one or more additives such as anticoagulants, lubricating agents, wetting agents, flavoring agents, emulsifiers, and preservatives.

For parenteral administration, the pharmaceutical composition of the present invention may be formulated with suitable carriers for parenteral administration into injectable preparations, preparations for transdermal administration, and nasal inhalers by suitable methods known in the art. The injectable preparations should be sterilized and protected from contamination by microorganisms such as bacteria and fungi. Examples of suitable carriers for the injectable preparations include, but are not limited to, water, ethanol, polyols (e.g., glycerol, propylene glycol, and liquid polyethylene glycol), mixtures thereof, and vegetable oil-containing solvents and dispersion media. Examples of more preferred carriers include Hank's solution, Ringer's solution, triethanolamine-containing phosphate buffered saline (PBS) and sterile water for injection, and isotonic solutions such as 10% ethanol, 40% propylene glycol, and 5% dextrose. The injectable preparations should be protected from microbial contamination. To this end, the injectable preparations may further include various antibacterial and antifungal agents such as paraben, chlorobutanol, phenol, sorbic acid, and thimerosal. In most cases, the injectable preparations may further include an isotonic agent such as sugar or sodium chloride.

For example, the preparations for transdermal administration may be in the form of ointments, creams, lotions, gels, solutions for external use, pastes, liniments or aerosols. The term "transdermal administration" refers to the topical administration of the pharmaceutical composition to the skin to deliver an effective amount of the active ingredient into the skin.

In the case of the preparations for inhalation, the active ingredient may be conveniently delivered in the form of an aerosol spray from a pressurized pack or nebulizer using a suitable propellant, for example, dichlorofluoromethane, trichlorofluoromethane, dichlorotetrafluoroethane, carbon dioxide or any other suitable gas. The dosage unit of the pressurized aerosol can be determined by providing a valve adapted to deliver a metered amount. For example, gelatin capsules and cartridges used for use in an inhaler or insufflator may be formulated to contain the active ingredient and a powder mixture based on a suitable powder such as lactose or starch. Formulations for parenteral administration can be found in the formulary known to all pharmaceutical chemists: "Remington's Pharmaceutical Science, 15th Edition, 1975. Mack Publishing Company, Easton, Pennsylvania 18042, Chapter 87: Blaug, Seymour".

The presence of an effective amount of the ganglioside in the pharmaceutical composition of the present invention can achieve the desired prophylactic or therapeutic effect for a muscle disease. As used herein, the term "effective amount" refers to an amount that results in achieving a better effect than that of the negative control, preferably an amount sufficient to improve muscle functions. The pharmaceutical composition of the present invention may include 0.01 to 99.99% of the ganglioside and a balance of one or more pharmaceutically acceptable carriers. The effective amount of the ganglioside in the pharmaceutical composition of the present invention may vary depending on the formulation of the composition, etc.

The total effective amount of the pharmaceutical composition according to the present invention can be administered to a patient as a single dose. Alternatively, the pharmaceutical composition of the present invention may be administered in multiple doses over a long period of time according to a fractionated treatment protocol. It is important to administer the pharmaceutical composition in the minimum amount that can exhibit the maximum effect without causing side effects, in view of all the above-described factors, and this amount can be easily determined by those skilled in the art.

The content of the active ingredient in the pharmaceutical composition of the present invention may vary depending on the severity of the disease. The pharmaceutical composition of the present invention is administered parenterally in an amount such that the daily dose of the ganglioside ranges from 0.01 to 50 mg/kg body weight, more preferably 0.1 and 30 mg/kg body weight. Meanwhile, the pharmaceutical composition of the present invention is administered orally in an amount such that the daily dose of the ganglioside ranges from 0.01 to 100 mg/kg body weight, more preferably 0.01 and 10 mg/kg body weight. The pharmaceutical composition of the present invention can be administered in single or divided doses. However, the effective dose of the ganglioside for a patient is determined taking into consideration various factors such as the age, body weight, general health, sex, and diet of the patient, the severity of the disease, and excretion rate as well as the route and frequency of administration of the pharmaceutical composition. In consideration of these factors, those skilled in the art can determine an appropriate effective dose of the ganglioside depending on the particular use for preventing or treating a muscle disease. The formulation, the route of administration, and the mode of administration of the pharmaceutical composition according to the present invention are not particularly limited as long as the effects of the present invention are produced.

The pharmaceutical composition of the present invention may be used alone or in combination with surgical therapy, radiotherapy, hormone therapy, chemotherapy or a biological response modifier.

The present invention also provides a cosmetic composition for preventing or ameliorating a muscle disease including a ganglioside as an active ingredient. The pharmaceutical composition and the cosmetic composition of the present invention can be provided in the form of external preparations.

The pharmaceutical composition and the cosmetic composition of the present invention can be used to provide external skin preparations. In this case, each composition may further include one or more adjuvants commonly used in the field of dermatology. Examples of suitable adjuvants include fatty substances, organic solvents, solubilizers, thickening agents, gelling agents, emollients, antioxidants, suspending agents, stabilizers, foaming agents, aromatic substances, surfactants, water, ionic emulsifiers, non-ionic emulsifiers, fillers, sequestering agents, chelating agents, preservatives, vitamins, blocking agents, wetting agents, essential oils, dyes, pigments, hydrophilic active agents, lipophilic active agents, lipid vesicles, and other ingredients commonly used in external skin preparations. These ingredients may be introduced in amounts commonly used in the field of dermatology.

The external skin preparations can be formulated into ointments, patches, gels, creams, and sprays but are not limited thereto.

The present invention also provides a food composition for preventing or ameliorating a muscle disease including a ganglioside as an active ingredient. The active ingredient ganglioside is effective in increasing muscle mass in a patient suffering from a muscle disease caused by muscle dysfunction, muscle wasting or muscle degeneration due to its ability to increase the expression and phosphorylation levels of proteins associated with muscle protein synthesis in muscle cells and an increase in muscle mass.

The food composition of the present invention can be used to prepare all types of foods, including functional foods, nutritional supplements, health foods, food additives, and feeds that can be eaten by animals, including humans or livestock. These types of foods can be prepared by suitable methods known in the art.

The food composition of the present invention can be processed into various forms by suitable methods known in the art. The food composition of the present invention can be added to general foods, including but not limited to, beverages (including alcoholic beverages), fruits and their processed foods (e.g., canned fruits, bottled fruits, jams, and marmalades), fish, meat and its processed foods (e.g., hams, sausages, and corned beef), breads and noodles (e.g., udon noodles, buckwheat noodles, ramens, spaghettis, and macaronis), fruit juices, drinks, cookies, taffies, dairy products (e.g., butters and cheeses), edible vegetable oils and fats, margarines, vegetable proteins, retort foods, frozen foods, and seasonings (e.g., soybean pastes, soy sauces, and spices). The food composition of the present invention can also be added to nutritional supplements in the form of capsules, tablets, and pills. However, the nutritional supplements are not limited to these formulations. The food composition of the present invention can also be applied to drinkable health beverages in the form of teas, juices, and drinks. To this end, the food composition of the present invention is processed into ingestible liquids, granules, capsules, and powders. The food composition of the present invention can also be used as a food additive. In this case, the food composition of the present invention is prepared in the form of a powder or concentrate. The food composition of the present invention can also be used in admixture with an active ingredient known to be effective in preventing a muscle disease and improving muscle functions.

For use in a health beverage, the food composition of the present invention may further include various flavoring agents or natural carbohydrates commonly used in beverages. The natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. The food composition of the present invention may use a natural sweetening agent such as thaumatin or *Stevia* extract or a synthetic sweetening agent such as saccharin or aspartame. The natural carbohydrates are typically used in a total amount of about 0.01 to about 0.04 g, preferably about 0.02 to about 0.03 g per 100 mL of the food composition.

The ganglioside as an active ingredient of the food composition of the present invention is used in an amount effective to prevent a muscle disease and improve muscle functions. The effective amount of the ganglioside is not particularly limited but is preferably 0.01 to 100% by weight, based on the total weight of the composition. The food composition of the present invention may be prepared by mixing the ganglioside with one or more other active ingredients known to be effective in preventing a muscle disease and improving muscle functions.

The present invention also provides a health food using the food composition. The health food of the present invention may further include one or more additives selected from nutrients, vitamins, electrolytes, flavoring agents, coloring agents, pectic acid and its salts, alginic acid and its salts, organic acids, protective colloidal thickeners, pH adjusting agents, stabilizers, preservatives, glycerin, alcohols, and carbonating agents. The health food of the present invention may further include flesh for the production of a natural fruit juice, fruit juice beverage or vegetable beverage. Such ingredients may be used independently or as a mixture thereof. The amounts of such additives are not critical but are typically in the range of 0.01 to 0.1 parts by weight, based on 100 parts by weight of the composition of the present invention.

The present invention will be more specifically explained with reference to the following examples, including production examples. However, it will be obvious to those skilled in the art that these examples are provided for illustrative purposes only and are not intended to limit the scope of the invention.

Example 1

Determination of Activity of Ganglioside GM3 for Myogenesis

The mTOR protein is known to induce the activation of proteins involved in muscle protein synthesis and an increase in muscle mass in the PI3K/Akt signaling pathway in muscle cells when phosphorylated and activated. Thus, the activity of mTOR was confirmed using an mTOR Sandwich ELISA kit (Cell Signaling Technology, Beverly, MA, USA) to determine the activity of ganglioside GM3 for myogenic induction.

L6 myoblasts (ATCC; Manassas, VA, USA) were seeded with Dulbecco's modified Eagle's media (DMEM; Hyclone) supplemented with 10% fetal bovine serum (FBS; Hyclone, Logan, UT, USA) in a 6-well plate at a density of 1×10$^5$ cells/well, followed by culture for 24 h. The media in the wells were replaced with DMEM (Hyclone) supplemented with 2% horse serum (HS; Hyclone), followed by culture for additional 6 days to differentiate the L6 cells into myotubes. Then, cells were treated with ganglioside GM3 (Cayman, Ann Arbor, MI, USA) at a concentration of 1 μM or 5 μM. After 12-h culture, cells were lysed by treatment with a cell lysis buffer. Proteins in the cell lysate were quantified by the Bradford method (Bio-Rad Laboratories Inc., Hercules, CA, USA) and the concentration of the cell lysate was then adjusted to 1 mg/mL. The cell lysate was plated in microwells bound with anti-mTOR antibody (50 μL/well) and cultured at 37° C. for 2 h. Cells were washed a total of 4 times with a washing buffer, treated with a detection antibody, and cultured at 37° C. for 1 h, rewashed a total of 4 times with a washing buffer, added with a horseradish peroxidase (HRP)-conjugated secondary antibody, and cultured at 37° C. for 30 min. Finally, after washing a total of 4 times with a washing buffer, TMB substrate was added to each well. After culture at 37° C. for 10 min, a stop solution was added to stop the TMB reaction. 2 min later, absorbance was measured at a wavelength of 450 nm to determine the level of mTOR in the myotubes treated with ganglioside GM3. The results are shown in FIG. 1.

As shown in FIG. 1, the treatment with ganglioside GM3 significantly increased the activity of mTOR in L6 muscle cells (*P<0.05), indicating that ganglioside GM3 has an outstanding ability to increase myogenesis in muscle cells.

Example 2

Determination of Activity of Ganglioside GM1 for Myogenesis

The procedure of Example 1 was repeated except that cells were treated with ganglioside GM1 (Cayman) at a concentration of 15 μM or 25 μM to examine the activity of the ganglioside for myogenic induction.

As shown in FIG. 2, the treatment with ganglioside GM1 significantly increased the activity of mTOR in L6 muscle cells (*P<0.05), indicating that ganglioside GM1 has an outstanding ability to increase myogenesis in muscle cells.

Example 3

Determination of Activity of Ganglioside GD1a for Myogenesis

The procedure of Example 1 was repeated except that cells were treated with ganglioside GD1a (Cayman) at a concentration of 1 μM or 3 μM to examine the activity of the ganglioside for myogenic induction.

As shown in FIG. 3, the treatment with ganglioside GD1a significantly increased the activity of mTOR in L6 muscle cells (*P<0.05), indicating that ganglioside GD1a has an outstanding ability to increase myogenesis in muscle cells.

Example 4

Determination of Activities of Gangliosides GT1b and GQ1b for Myogenesis

The procedure of Example 1 was repeated except that cells were treated with each of gangliosides GT1b and GQ1b (Cayman) at a concentration of 1 μM to examine the activity of the ganglioside for myogenic induction.

As shown in FIG. 4, the treatment with each of gangliosides GT1b and GQ1b significantly increased the activity of mTOR in L6 muscle cells (*P<0.05), indicating that each of gangliosides GT1b and GQ1b has an outstanding ability to increase myogenesis in muscle cells.

Example 5

Determination of Promoting Effect of Ganglioside GM3 on mRNA Translation Activity in Muscle Cells L6 myoblasts (ATCC) were seeded with DMEM (Hyclone) supplemented with 10% FBS (Hyclone) in a 6-well plate at a density of 1×10$^5$ cells/well, followed by culture. When the cultured cells reached a confluency of ~80-85% per well, the media in the wells were replaced with DMEM (Hyclone) supplemented with 2% HS (Hyclone), followed by culture for additional 6 days to induce differentiation into myotubes. During culture for 6 days, the culture media were changed once every other day a total of 3 times. The differentiation-induced cells were harvested and the cell media were replaced with DMEM supplemented with 50 ng/mL tumor necrosis factor alpha (TNF-α; PeproTech, Rocky Hills, NJ, USA) in which ganglioside GM3 (Cayman) was dissolved at a concentration of 1 µM or 5 µM. A group treated with 0.01% DMSO instead of the sample was used as a control. Cells were lysed with NP-40 buffer (ELPIS-Biotech, Daej eon, Korea) with a protease inhibitor cocktail (Sigma-Aldrich, St. Louis, MO, USA) and centrifuged at 13,000 rpm for 10 min. The cell lysate was obtained from the supernatant. The concentration of proteins in the supernatant was determined by the Bradford method (Bio-Rad Laboratories Inc.). Proteins at a certain concentration were heated for 5 min and separated by SDS-PAGE electrophoresis. The separated proteins were transferred to nitrocellulose membranes. Then, p-mTOR, mTOR, p-p70S6K, p70S6K, p-4EBP1, 4EBP1, and alpha-tubulin primary antibodies (Cell signaling technology, Beverly, MA, USA) were diluted at a ratio of 1:1000 with 2.5% bovine serum albumin (BSA; Bioworld, Dubin, OH, USA) and incubated with the proteins transferred to the nitrocellulose membranes at room temperature for 20 h. After incubation of the primary antibodies, the nitrocellulose membranes were washed 3 times with Tris-buffer saline Tween 20 (TBST) for 10 min. After washing, an anti-rabbit secondary antibody (Bethyl Laboratories, Inc., Montgomery, TA, USA) conjugated with horseradish peroxidase recognizing the primary antibodies was diluted 1:5000 with 2.5% BSA (Bioworld) and incubated with the nitrocellulose membranes at room temperature for 2 h. The nitrocellulose membranes were washed 3 times with TBST for 10 min.

Protein bands detected through antibody binding were developed using an ECL western blot detection reagent (Amersham, Tokyo, Japan) and visualized using a G;BOX EF imaging system (Syngene, Cambridge, UK).

As shown in FIG. 5, the treatment with ganglioside GM3 increased the expression levels of the phosphorylated p-mTOR, p-P70S6K, and p-4EBP1 in L6 muscle cells, indicating that ganglioside GM3 is highly effective in increasing myogenesis in muscle cells.

Example 6

Determination of Promoting Effect of Ganglioside GM1 on mRNA Translation Activity in Muscle Cells The procedure of Example 5 was repeated except that cells were treated with ganglioside GM1 (Cayman) at a concentration of 15 µM or 25 µM to evaluate the activities of p-mTOR, p-P70S6K, and p-4EBP1.

As shown in FIG. 6, the treatment with ganglioside GM1 increased the expression levels of the phosphorylated p-mTOR, p-P70S6K, and p-4EBP1 in L6 muscle cells, indicating that ganglioside GM1 is highly effective in increasing myogenesis in muscle cells.

Example 7

Determination of Promoting Effect of Ganglioside GD1a on mRNA Translation Activity in Muscle Cells The procedure of Example 5 was repeated except that cells were treated with ganglioside GD1a (Cayman) at a concentration of 1 µM or 3 µM to evaluate the activities of p-mTOR, p-P70S6K, and p-4EBP1.

As shown in FIG. 7, the treatment with ganglioside GD1a increased the expression levels of the phosphorylated p-mTOR, p-P70S6K, and p-4EBP1 in L6 muscle cells, indicating that ganglioside GD1a is highly effective in increasing myogenesis in muscle cells.

Example 8

Determination of Inhibitory Effect of Ganglioside GM3 on Muscle Protein Degradation in Muscle Cells Since ganglioside GM3 was demonstrated to be effective in increasing myogenesis in muscle cells, the mRNA transcription and expression levels of atrogin-1 and MuRF1 as muscle degrading proteins were investigated to determine whether newly produced muscle proteins were also protected due to the inhibitory activity of ganglioside GM3 on protein degradation.

L6 myoblasts (ATCC) were seeded with DMEM (Hyclone) supplemented with 10% FBS (Hyclone) in a 6-well plate at a density of $1 \times 10^5$ cells/well, followed by culture. When the cultured cells reached a confluency of ~80-85% per well, the media in the wells were replaced with DMEM (Hyclone) supplemented with 2% HS (Hyclone), followed by culture for additional 6 days to induce differentiation into myotubes. During culture for 6 days, the culture media were changed once every other day a total of 3 times. The differentiation-induced cells were harvested and the cell media were replaced with DMEM supplemented with 50 ng/mL TNF-α (PeproTech) in which ganglioside GM3 (Cayman) was dissolved at a concentration of 1 µM or 5 µM. A group treated with 0.01% DMSO instead of the sample was used as a control. Total RNA was isolated from cells using TRIzol reagent (Takara, Kyoto, Japan). The isolated total RNA was quantified using NanoDrop 1000 (Thermo Fisher Scientific Inc., Waltham, MA, USA). 16 µL of the RNA was synthesized into cDNA using Reverse Transcriptase Premix (ELPIS-Biotech) and a PCR system (Gene Amp PCR System 2700; Applied Biosystems, Foster City, CA, USA) at 42° C. for 55 min and 70° C. for 15 min. 3 µL of the synthesized cDNA, the specific primers shown in Table 1 (Bioneer, Daej eon, Korea), and PCR premix (ELPIS-Biotech) were mixed and PCR was repeated 30 times at 95° C. for 30 sec, 60° C. for 1 min, and 72° C. for 1 min. After PCR amplification, cDNA was separated by electrophoresis on a 1.5% agarose gel and the cDNA bands were visualized using a G;BOX EF imaging system (Syngene).

TABLE 1

| Primer name | Direction | Sequence | SEQ ID NO: |
|---|---|---|---|
| Atrogin-1_F | Forward | 5'-TGGATACTGCACTTTGGGGG-3' | SEQ ID NO: 1 |
| Atrogin-1_R | Reverse | 5'-GGACCAGCGTGCATAAGGAT-3' | SEQ ID NO: 2 |
| MuRF1_F | Forward | 5'-CCGGACGGAAATGCTATGGA-3' | SEQ ID NO: 3 |
| MuRF1_R | Reverse | 5'-AGCCTGGAAGATGTCGTTGG-3' | SEQ ID NO: 4 |

TABLE 1-continued

| Primer name | Direction | Sequence | SEQ ID NO: |
|---|---|---|---|
| β-Actin_F | Forward | 5'-CGAGTACAACCTTCTTGCAGCTC-3' | SEQ ID NO: 5 |
| β-Actin_R | Reverse | 5'-CCAAATCTTCTCCATATCGTCCCAG-3' | SEQ ID NO: 6 |

As shown in FIG. 8, the treatment with ganglioside GM3 reduced the mRNA expression levels of the muscle degrading proteins atrogin-1 and MuRF1 in L6 muscle cells, indicating that ganglioside GM3 has an outstanding ability to inhibit muscle protein degradation in muscle cells.

Example 9

Determination of Inhibitory Effect of Ganglioside GM1 on Muscle Protein Degradation in Muscle Cells The procedure of Example 8 was repeated except that cells were treated with ganglioside GM1 (Cayman) at a concentration of 15 µM or 25 µM to investigate the mRNA transcription and expression levels of atrogin-1 and MuRF1 as muscle degrading proteins.

As shown in FIG. 9, the treatment with ganglioside GM1 reduced the mRNA expression levels of the muscle protein degradation-related enzymes atrogin-1 and MuRF1 in L6 muscle cells, indicating that ganglioside GM1 has an outstanding ability to inhibit muscle protein degradation in muscle cells.

Example 10

Determination of Inhibitory Effect of Ganglioside GD1a on Muscle Protein Degradation in Muscle Cells The procedure of Example 8 was repeated except that cells were treated with ganglioside GD1a (Cayman) at a concentration of 1 µM or 3 µM to investigate the mRNA transcription and expression levels of atrogin-1 and MuRF1 as muscle protein degradation-related enzymes.

As shown in FIG. 10, the treatment with ganglioside GD1a reduced the mRNA expression levels of the muscle protein degradation-related enzymes atrogin-1 and MuRF1 in L6 muscle cells, indicating that ganglioside GD1a has an outstanding ability to inhibit muscle protein degradation in muscle cells.

Example 11

Determination of Inhibitory Effects of Gangliosides GT1b and GQ1b on Muscle Protein Degradation in Muscle Cells The procedure of Example 8 was repeated except that cells were treated with each of gangliosides GT1b and GQ1b (Cayman) at a concentration of 1 µM to investigate the mRNA transcription and expression levels of atrogin-1 and MuRF1 as muscle protein degradation-related enzymes.

As shown in FIG. 11, the treatment with each of gangliosides GT1b and GQ1b reduced the mRNA expression levels of the muscle protein degradation-related enzymes atrogin-1 and MuRF1 in L6 muscle cells, indicating that each of gangliosides GT1b and GQ1b has an outstanding ability to inhibit muscle protein degradation in muscle cells.

Example 12

Determination of Increasing Effects of Gangliosides GM3, GM1, GD1a, GT1b, and GQ1b on Muscle Mass in Animal Models Wistar rats, aged five weeks, were acclimatized for one week and supplied with 100 ng/g of TNF-α for 2 weeks to induce muscular atrophy. The animals were randomly divided into a total of 5 groups, 8 animals per group, depending on their weight. Each of gangliosides GM3, GM1, GD1a, GT1b, and GQ1b (each 50 mg/kg body weight) as experimental groups was suspended in 0.25% carboxymethylcellulose. The suspension was administered at a given time once a day for 8 weeks. A group administered the same amounts of 0.25% carboxymethyl cellulose and TNF-α ingested by each experimental group was used as a control.

After administration of the sample for 8 weeks, the right soleus was dissected and its weight was measured with a microbalance (Mettler PE160, USA). The results are shown in Table 2. The muscle weights of the groups administered gangliosides GM3, GM1, GD1a, GT1b, and GQ1b were significantly increased by 23.56% ($P<0.01$), 22.11% ($P<0.01$), 17.79% (*$P<0.05$), 14.42% (*$P<0.05$), and 16.37% (*$P<0.05$), respectively, compared to that of the control group. These results demonstrate that the gangliosides efficiently increase muscle mass.

TABLE 2

| Experimental group | Average soleus weight (mg) |
|---|---|
| Control | 416.0 ± 19.57 |
| Ganglioside GM3 | 514.0 ± 18.4** |
| Ganglioside GM1 | 508.0 ± 19.8** |
| Ganglioside GD1a | 490.0 ± 22.8* |
| Ganglioside GT1b | 476.0 ± 24.1* |
| Ganglioside GQ1b | 484.1 ± 25.4* |

The production of pharmaceuticals and foods including gangliosides as active ingredients will be specifically explained with reference to the following production examples. However, these examples are not intended to limit the invention. Pharmaceuticals (Production Example 1) and foods (Production Example 2) having the compositions shown below were produced according to suitable methods known in the art. Gangliosides used as active ingredients are known to be effective in preventing or treating muscle diseases or improving muscle functions.

<Production Example 1> Production of Pharmaceutical Preparations

<1-1> Production of Powders

| | |
|---|---|
| Ganglioside | 0.1 g |
| Lactose | 1.5 g |
| Talc | 0.5 g |

The ingredients were mixed and filled in airtight bags to produce powders.

<1-2> Production of Tablets

| Ganglioside | 0.1 g |
|---|---|
| Lactose | 7.9 g |
| Crystalline cellulose | 1.5 g |
| Magnesium stearate | 0.5 g |

The ingredients were mixed and compressed into tablets by a direct tableting method.

<1-3> Production of Capsules

| Ganglioside | 0.1 g |
|---|---|
| Corn starch | 5 g |
| Carboxycellulose | 4.9 g |

The ingredients were mixed and filled in hard capsules to produce capsules in accordance with a general method known in the art.

<1-4> Production of Injectable Preparations

| Ganglioside | 0.1 g |
|---|---|
| Sterile distilled water for injection | Appr. amount |
| pH adjusting agent | Appr. amount |

In accordance with a general method known in the art, the ingredients were mixed and filled in ampoules to produce injectable preparations (2 ml/ampoule).

<1-5> Production of Liquid Preparations

| Ganglioside | 0.1 g |
|---|---|
| Isomerized glucose syrup | 10 g |
| Mannitol | 5 g |
| Purified water | Appr. amount |

In accordance with a general method known in the art, the ingredients were dissolved in purified water, an appropriate amount of lemon flavor was added to the solution, the weight was adjusted to a total of 100 g with purified water, and the mixture was filled in amber glass bottles and sterilized to produce liquid preparations.

<Production Example 2> Production of Foods

<2-1> Production of Wheat Flour Foods 0.5-5.0 parts by weight of the ganglioside was added to wheat flour, and the mixture was used to produce breads, cakes, cookies, crackers, and noodles.

<2-2> Production of Soups and Gravies

Soups and gravies for processed meat products and noodles for health improvement were produced by addition of the ganglioside. 0.5-5.0 parts by weight of the ganglioside was used for each of the soups and gravies.

<2-3> Production of Ground Beefs

Ground beefs for health improvement were produced by addition of the ganglioside. 0.5-5.0 parts by weight of the ganglioside was used for each of the ground beefs.

<2-4> Production of Dairy Products 5-10 parts by weight of the ganglioside was added to milk, and the mixture was used to produce dairy products, including butters and ice creams.

<2-5> Production of Health Supplement Foods

| Ganglioside | 100 mg |
|---|---|
| Vitamin mixture | Appr. amount |
| Vitamin A Acetate | 70 µg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinamide | 1.7 mg |
| Folic acid | 50 µg |
| Calcium pantothenate | 0.5 mg |
| Mineral mixture | Appr. amount |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The compositions of the vitamin mixture and the mineral mixture were prepared by mixing relatively suitable components for health foods but could be changed arbitrarily. The components were mixed and granulated in accordance with a general method for preparing health foods. The granules can be used to prepare health food compositions in accordance with a general method known in the art.

<2-6> Production of Health Beverages

| Ganglioside | 100 mg |
|---|---|
| Citric acid | 100 mg |
| Oligosaccharides | 100 mg |
| Plum concentrate | 2 mg |
| Taurine | 100 mg |
| Purified water | Up to a total of 500 mL |

In accordance with a general method known in the art, the ingredients were mixed, heated with stirring at 85° C. for ~1 h, filtered, filled in a sterilized 1 L container, sealed, sterilized, and kept refrigerated. The mixture was used to prepare a composition for health beverages.

The composition was prepared by mixing relatively suitable components for desired beverages but could be changed arbitrarily according to the regional and ethnic preferences of consumers such as demand classes, demand nations, and purposes of use.

INDUSTRIAL APPLICABILITY

As described above, the compositions of the present invention, each of which includes a ganglioside as an active ingredient, are effective in preventing or treating a muscle disease or improving muscle functions. More specifically, the gangliosides have the ability to increase the expression of proteins associated with muscle protein synthesis in muscle cells and an increase in muscle mass and inhibit the expression of enzymes involved in muscle protein degradation at the mRNA level, thus being very effective in preventing or treating a muscle disease or improving muscle functions. The use of the gangliosides is safe without side effects and makes the compositions highly effective in preventing or treating a muscle disease or improving muscle functions. Therefore, the present invention is expected to be useful for industrial applications.

We claim:
1. A method of increasing mRNA expression levels of mTOR and reducing mRNA expression levels of atrogin-1 and MuRF1 in muscle cells for treating cachexia or age-related sarcopenia in a subject in need thereof, comprising administering a pharmaceutical composition comprising a ganglioside as an active ingredient,
wherein the ganglioside of the pharmaceutical composition is obtainable from antler, sweet potato, colostrum, milk, or a mixture thereof,
wherein the ganglioside is selected from the group consisting of ganglioside GM1, ganglioside GD1a, ganglioside GT1b, and ganglioside GQ1b,
wherein the ganglioside GM1 is represented by Formula 3, wherein the ganglioside GD1a is represented by Formula 4, wherein the ganglioside GT1b is represented by Formula 5, wherein the ganglioside GQ1b is represented by Formula 6,

[Formula 3]

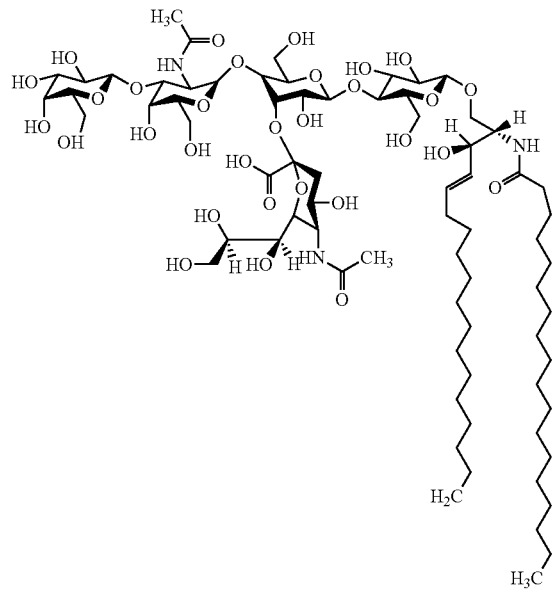

[Formula 4]

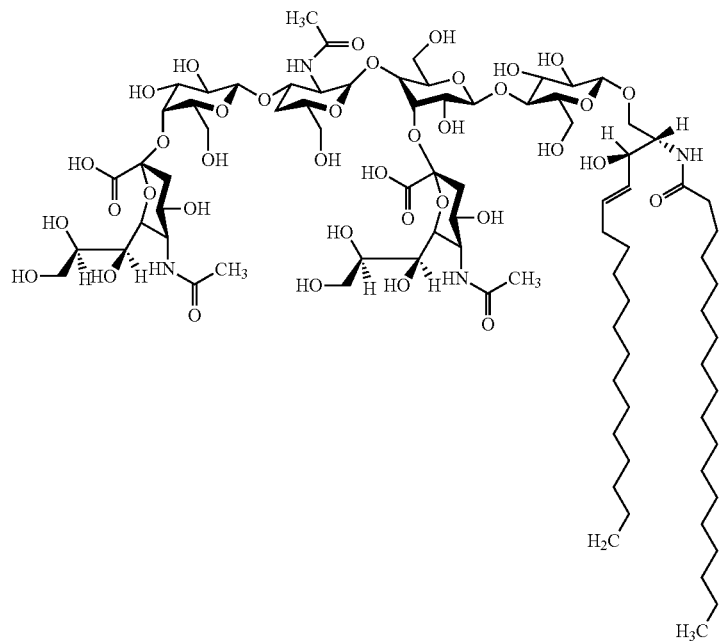

-continued
[Formula 5]
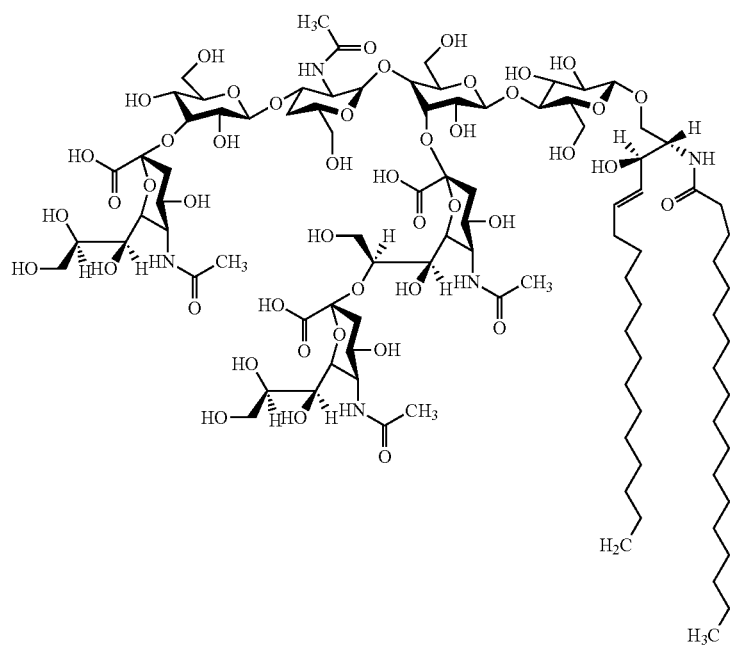
[Formula 6]
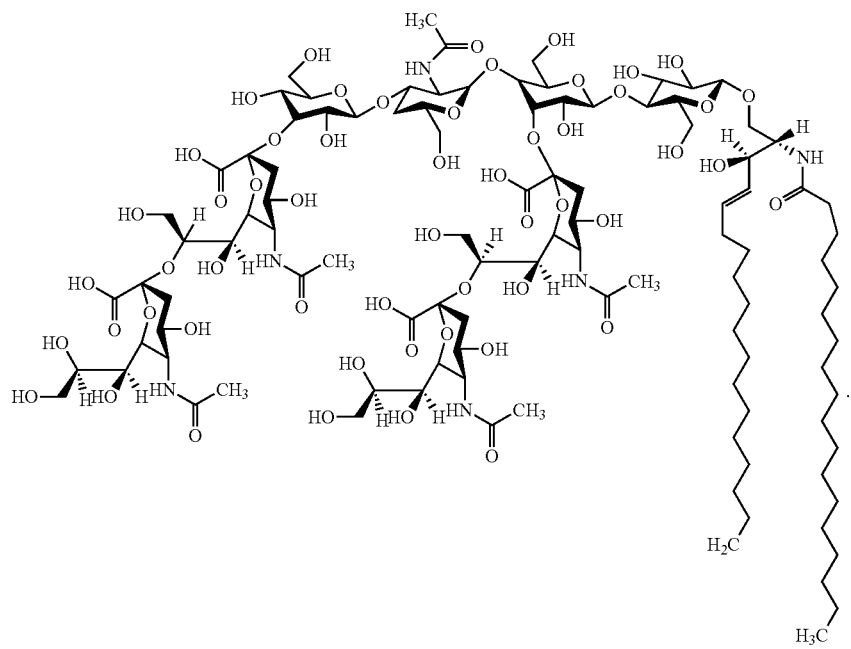
2. The method according to claim 1, wherein the daily dose of the ganglioside is 50 mg/kg of body weight.
3. The method according to claim 1, wherein the daily dose of the ganglioside is 100 mg/kg of body weight.
* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Atrogin-1 forward primer

<400> SEQUENCE: 1
tggatactgc actttggggg                                               20

<210> SEQ ID NO 2
<211> LENGTH: 20
<212> TYPE: DNA
<213> ORGANISM: Artificial Sequence
<220> FEATURE:
<223> OTHER INFORMATION: Atrogin-1 reverse primer

<400> SEQUENCE: 2
ggaccagcgt gcataaggat                                               20

<210> SEQ ID NO 3
<211> LENGTH: 20
<212> TYPE: DNA
<213> ORGANISM: Artificial Sequence
<220> FEATURE:
<223> OTHER INFORMATION: MuRF1 forward primer

<400> SEQUENCE: 3
ccggacggaa atgctatgga                                               20

<210> SEQ ID NO 4
<211> LENGTH: 20
<212> TYPE: DNA
<213> ORGANISM: Artificial Sequence
<220> FEATURE:
<223> OTHER INFORMATION: MuRF1 reverse primer

<400> SEQUENCE: 4
agcctggaag atgtcgttgg                                               20

<210> SEQ ID NO 5
<211> LENGTH: 23
<212> TYPE: DNA
<213> ORGANISM: Artificial Sequence
<220> FEATURE:
<223> OTHER INFORMATION: beta-Actin forward primer

<400> SEQUENCE: 5
cgagtacaac cttcttgcag ctc                                           23

<210> SEQ ID NO 6
<211> LENGTH: 25
<212> TYPE: DNA
<213> ORGANISM: Artificial Sequence
<220> FEATURE:
<223> OTHER INFORMATION: beta-Actin reverse primer

<400> SEQUENCE: 6
ccaaatcttc tccatatcgt cccag                                         25
```